(12) United States Patent
Chen et al.

(10) Patent No.: US 6,764,477 B1
(45) Date of Patent: Jul. 20, 2004

(54) CENTER-FILL ABSORBENT ARTICLE WITH REUSABLE FRAME MEMBER

(75) Inventors: Fung-jou Chen, Appleton, WI (US); Jeffrey Dean Lindsay, Appleton, WI (US); Julie Marie Bednarz, Neenah, WI (US); Margaret Gwyn Latimer, Alpharetta, GA (US); Joseph DiPalma, Neenah, WI (US); Teresa Marie Zander, Bonduel, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/410,997

(22) Filed: Oct. 1, 1999

(51) Int. Cl.$^7$ .................................................. A61F 13/15
(52) U.S. Cl. .............. 604/385.14; 604/393; 604/385.19
(58) Field of Search ............................ 604/393, 385.01, 604/397, 398, 402, 385.19, 385.13, 385.14, 385.11, 385.23, 395

(56) References Cited

U.S. PATENT DOCUMENTS

| | | |
|---|---|---|
| 2,064,431 A | 12/1936 | Jurgensen |
| 2,683,457 A | 7/1954 | Cunningham |
| 2,747,575 A | 5/1956 | Mercer |
| 3,126,888 A | 3/1964 | Woldman |
| 3,156,242 A | 11/1964 | Crowe, Jr. |
| 3,294,091 A | 12/1966 | Morse |
| 3,575,174 A | 4/1971 | Mogor |
| 3,667,466 A | 6/1972 | Ralph |
| 3,860,003 A | 1/1975 | Buell |
| 3,881,489 A | 5/1975 | Hartwell |
| 3,881,491 A | 5/1975 | Whyte |
| 3,921,232 A | 11/1975 | Whyte |
| 3,989,867 A | 11/1976 | Sisson |
| 4,015,604 A | 4/1977 | Csillag |
| 4,100,324 A | 7/1978 | Anderson et al. |
| 4,195,634 A | 4/1980 | DiSalvo et al. |
| 4,247,362 A | 1/1981 | Williams |
| 4,285,343 A | 8/1981 | McNair |
| 4,324,246 A | 4/1982 | Mullane et al. |
| 4,342,314 A | 8/1982 | Radel et al. |
| 4,397,644 A | 8/1983 | Matthews et al. |
| 4,405,326 A | 9/1983 | Lenaghan |
| 4,421,812 A | 12/1983 | Plant |
| 4,425,130 A | 1/1984 | DesMarais |
| 4,463,045 A | 7/1984 | Ahr et al. |
| 4,476,180 A | 10/1984 | Wnuk |
| 4,480,516 A | 11/1984 | Leroy |
| 4,490,147 A | 12/1984 | Pierce et al. |

(List continued on next page.)

FOREIGN PATENT DOCUMENTS

| | | |
|---|---|---|
| AU | 699325 | 12/1998 |
| CA | 884608 | 11/1971 |
| DE | 196 40 451 A1 | 4/1998 |

(List continued on next page.)

OTHER PUBLICATIONS

AATCC Test Method 127–1977, "Water Resistance: Hydrostatic Pressure Test," Technical Manual of the American Association of Textile Chemists and Colorists, reaffirmed 1977, p. 242.

(List continued on next page.)

Primary Examiner—John J. Calvert
Assistant Examiner—Jacqueline F Stephens
(74) Attorney, Agent, or Firm—Pauley Petersen & Erickson

(57) ABSTRACT

A composite absorbent article comprises a reusable frame member for shaping and leakage control onto which a single-use absorbent device can be detachably connected and repeatedly replaced without the need to replace the reusable frame member. A low-cost, high-performance composite absorbent article can thus be provided from low-cost single-use absorbent devices by virtue of the reusable frame member. A wicking barrier lining a central void or depression helps provide leakage containment for the overall composite absorbent article.

67 Claims, 5 Drawing Sheets

U.S. PATENT DOCUMENTS

| | | |
|---|---|---|
| 4,496,359 A | 1/1985 | Pigneul |
| 4,536,181 A | 8/1985 | Cook |
| 4,556,146 A | 12/1985 | Swanson et al. |
| 4,556,560 A | 12/1985 | Buckingham |
| 4,573,986 A | 3/1986 | Minetola et al. |
| 4,576,596 A | 3/1986 | Jackson et al. |
| 4,576,597 A | 3/1986 | Hlaban et al. |
| 4,578,070 A | 3/1986 | Holtman |
| 4,589,876 A | 5/1986 | Van Tilburg |
| 4,608,047 A | 8/1986 | Mattingly |
| 4,654,040 A | 3/1987 | Luceri |
| 4,655,759 A | 4/1987 | Romans-Hess et al. |
| 4,662,876 A | 5/1987 | Wiegner |
| 4,687,478 A | 8/1987 | Van Tilburg |
| 4,701,177 A | 10/1987 | Ellis et al. |
| RE32,649 E | 4/1988 | Brandt et al. |
| 4,738,677 A | 4/1988 | Foreman |
| 4,753,644 A | 6/1988 | Cottenden et al. |
| 4,753,645 A * | 6/1988 | Johnson |
| 4,758,240 A | 7/1988 | Glassman |
| 4,804,380 A | 2/1989 | Lassen et al. |
| 4,846,824 A | 7/1989 | Lassen et al. |
| 4,879,170 A | 11/1989 | Radwanski et al. |
| 4,886,513 A | 12/1989 | Mason, Jr. et al. |
| 4,936,839 A | 6/1990 | Molee et al. |
| 4,950,264 A | 8/1990 | Osborn, III |
| 4,961,736 A | 10/1990 | McCloud |
| 4,964,857 A | 10/1990 | Osborn |
| 4,973,325 A | 11/1990 | Sherrod et al. |
| 5,007,906 A | 4/1991 | Osborn, III et al. |
| 5,009,653 A | 4/1991 | Osborn, III |
| 5,030,314 A | 7/1991 | Lang |
| 5,147,343 A | 9/1992 | Kellenberger |
| 5,147,345 A | 9/1992 | Young et al. |
| 5,151,092 A | 9/1992 | Buell et al. |
| 5,188,625 A | 2/1993 | Van Iten et al. |
| 5,217,445 A | 6/1993 | Young et al. |
| 5,217,447 A | 6/1993 | Gagnon |
| 5,219,342 A | 6/1993 | Hatch et al. |
| 5,235,515 A | 8/1993 | Ungpiyakul et al. |
| 5,236,428 A | 8/1993 | Zajaczkowski |
| 5,267,992 A | 12/1993 | Van Tilburg |
| 5,300,055 A | 4/1994 | Buell |
| 5,308,346 A | 5/1994 | Sneller et al. |
| 5,324,278 A | 6/1994 | Visscher et al. |
| 5,324,575 A | 6/1994 | Sultze et al. |
| 5,342,337 A | 8/1994 | Runeman et al. |
| 5,342,342 A | 8/1994 | Kitaoka |
| 5,350,624 A | 9/1994 | Georger et al. |
| 5,354,400 A | 10/1994 | Lavash et al. |
| 5,360,420 A | 11/1994 | Cook et al. |
| 5,360,422 A * | 11/1994 | Brownlee et al. ...... 604/385.15 |
| 5,389,094 A | 2/1995 | Lavash et al. |
| 5,399,175 A | 3/1995 | Glaug et al. |
| 5,399,412 A | 3/1995 | Sudall et al. |
| 5,401,267 A | 3/1995 | Couture-Dorschner et al. |
| 5,405,342 A * | 4/1995 | Roessler et al. |
| 5,413,568 A | 5/1995 | Roach et al. |
| 5,415,643 A | 5/1995 | Kolb |
| 5,429,628 A | 7/1995 | Trinh et al. |
| 5,429,629 A | 7/1995 | Latimer et al. |
| 5,429,630 A | 7/1995 | Beal et al. |
| 5,445,628 A | 8/1995 | Gipson et al. |
| 5,447,507 A | 9/1995 | Yamamoto |
| 5,462,166 A | 10/1995 | Minton et al. |
| 5,476,457 A | 12/1995 | Roessler et al. |
| 5,487,736 A | 1/1996 | Van Phan |
| 5,489,283 A | 2/1996 | Van Tillburg |
| 5,506,035 A | 4/1996 | Van Phan et al. |
| 5,514,104 A | 5/1996 | Cole et al. |
| 5,518,801 A | 5/1996 | Chappell et al. |
| 5,520,674 A | 5/1996 | Lavon et al. |
| 5,533,991 A | 7/1996 | Kirby et al. |
| 5,542,941 A | 8/1996 | Morita |
| 5,545,156 A | 8/1996 | DiPalma et al. |
| 5,547,745 A | 8/1996 | Hansen et al. |
| 5,562,645 A | 10/1996 | Tanzer et al. |
| 5,562,650 A | 10/1996 | Everett et al. |
| 5,567,260 A | 10/1996 | McFall |
| 5,575,785 A | 11/1996 | Gryskiewicz et al. |
| 5,591,146 A | 1/1997 | Hasse |
| 5,591,148 A | 1/1997 | McFall et al. |
| 5,591,150 A | 1/1997 | Olsen et al. |
| 5,599,339 A | 2/1997 | Horney |
| 5,601,544 A | 2/1997 | Glaug et al. |
| 5,611,790 A | 3/1997 | Osborn, III et al. |
| 5,618,282 A | 4/1997 | Schlangen |
| 5,620,430 A | 4/1997 | Bamber |
| 5,624,423 A | 4/1997 | Anjur et al. |
| 5,649,917 A | 7/1997 | Roberts et al. |
| 5,672,248 A | 9/1997 | Wendt et al. |
| 5,692,939 A | 12/1997 | DesMarais |
| 5,693,411 A | 12/1997 | Hansen et al. |
| 5,702,378 A | 12/1997 | Widlund et al. |
| 5,704,928 A | 1/1998 | Morita et al. |
| 5,704,930 A | 1/1998 | Lavash et al. |
| 5,704,932 A | 1/1998 | Hibbard |
| 5,711,970 A | 1/1998 | Lau et al. |
| 5,720,738 A | 2/1998 | Clark |
| 5,725,821 A | 3/1998 | Gannon et al. |
| 5,746,729 A | 5/1998 | Wada et al. |
| 5,753,343 A | 5/1998 | Braun et al. |
| 5,766,213 A | 6/1998 | Hackman et al. |
| 5,769,834 A | 6/1998 | Reiter et al. |
| 5,772,967 A | 6/1998 | Wannlund et al. |
| 5,773,120 A | 6/1998 | Deka et al. |
| 5,779,860 A | 7/1998 | Hollenberg et al. |
| 5,795,921 A | 8/1998 | Dyer et al. |
| 5,797,347 A * | 8/1998 | Ochi |
| 5,800,417 A | 9/1998 | Goerg-Wood et al. |
| 5,810,798 A * | 9/1998 | Finch et al. |
| 5,817,079 A | 10/1998 | Bergquist et al. |
| 5,817,081 A | 10/1998 | LaVon et al. |
| 5,817,394 A | 10/1998 | Alikhan et al. |
| 5,820,616 A | 10/1998 | Horney |
| 5,820,620 A * | 10/1998 | Allison-Rogers |
| 5,824,004 A | 10/1998 | Osborn, III et al. |
| 5,846,230 A | 12/1998 | Osborn, III et al. |
| 5,851,648 A | 12/1998 | Stone et al. |
| 5,853,867 A | 12/1998 | Harada et al. |
| 5,858,011 A | 1/1999 | Brown et al. |
| 5,858,021 A | 1/1999 | Sun et al. |
| 5,865,824 A | 2/1999 | Chen et al. |
| 5,869,033 A | 2/1999 | Schulz |
| 5,874,070 A | 2/1999 | Trinh et al. |
| 5,874,071 A | 2/1999 | Yu et al. |
| 5,876,393 A | 3/1999 | Ahr et al. |
| 5,910,137 A | 6/1999 | Clark et al. |
| 5,954,705 A | 9/1999 | Sawaki et al. |
| 5,957,909 A | 9/1999 | Hammons et al. |
| 5,990,377 A | 11/1999 | Chen et al. |
| 6,011,195 A * | 1/2000 | Muhs et al. |
| 6,017,336 A * | 1/2000 | Sauer |
| 6,022,338 A * | 2/2000 | Putzer |
| 6,277,105 B1 * | 8/2001 | Rynish |
| 6,623,466 B1 * | 9/2003 | Richardson ............ 604/385.19 |

FOREIGN PATENT DOCUMENTS

| | | |
|---|---|---|
| EP | 0136524 A1 | 4/1985 |
| EP | 0360285 A2 | 3/1990 |
| EP | 0 400 895 A1 | 12/1990 |

| | | | |
|---|---|---|---|
| EP | 0520884 | A1 | 12/1992 |
| EP | 0 117 613 | B2 | 3/1993 |
| EP | 0 564 307 | A1 | 10/1993 |
| EP | 0687453 | A1 | 12/1995 |
| EP | 0 612 233 | B1 | 4/1996 |
| EP | 0 552 345 | B1 | 9/1996 |
| EP | 0 516 964 | B1 | 11/1996 |
| EP | 0758543 | A1 | 2/1997 |
| EP | 0768070 | A1 | 4/1997 |
| EP | 0 638 303 | B1 | 11/1997 |
| EP | 0804914 | A1 | 11/1997 |
| EP | 0815817 | A1 | 1/1998 |
| EP | 0 652 736 | B1 | 10/1998 |
| EP | 0868894 | A1 | 10/1998 |
| EP | 0 419 434 | B2 | 11/1998 |
| EP | 0 758 220 | B1 | 12/1998 |
| EP | 0 893 517 | A2 | 1/1999 |
| EP | 0945110 | A2 | 9/1999 |
| GB | 2168612 | A | 6/1986 |
| GB | 2306333 | A | 5/1997 |
| WO | WO 83/03051 | A1 | 9/1983 |
| WO | WO 92/07535 | A1 | 5/1992 |
| WO | WO 93/21879 | A1 | 11/1993 |
| WO | WO 94/24973 | A1 | 11/1994 |
| WO | WO 95/24878 | A1 | 9/1995 |
| WO | WO 97/19808 | A1 | 6/1997 |
| WO | WO 97/24283 | A1 | 7/1997 |
| WO | WO 98/22059 | A1 | 5/1998 |
| WO | WO 98/24391 | A2 | 6/1998 |
| WO | WO 98/43684 | A1 | 10/1998 |
| WO | WO 99/00093 | A1 | 1/1999 |
| WO | WO 99/12502 | A1 | 3/1999 |
| WO | WO 00/19955 | A2 | 4/2000 |
| WO | WO 00/19956 | A1 | 4/2000 |
| ZA | 98/4033 | | 5/1998 |

OTHER PUBLICATIONS

American Society for Testing Materials (ASTM) Designation: D 3574–91, "Standard Test Methods for Flexible Cellular Materials—Slab, Bonded, and Molded Urethane Foams," pp. 303–319, published Mar. 1992.

American Society for Testing Materials (ASTM) Designation: D 4032–82, "Standard Test Method for Stiffness of Fabric by the Circular Bend Procedure," pp. 702–706, published Aug. 1982.

Federal Specification UU–T–595b, "Towel, Wiping, Paper: Industrial And Institutional," Apr. 4, 1967, 8 pages.

Federal Specification UU–T–595c, "Towel, Wiping, Paper: Industrial And Institutional," Jul. 27, 1976, 8 pages.

Gibson, P.W. et al., "Electrospun Fiber Mats: Transport Properties," AIChE Journal, vol. 45, No. 1, Jan. 1999, pp. 190–195.

Kim, S.H. et al., "Synthesis and Characterization of Dextran–Based Hydrogel Prepared By Photocrosslinking," Carbohydrate Polymers, vol. 40, No. 3, Sep. 1999, pp. 183–190.

Krema, Radko et al., "What's New in Highloft Production?" Nonwovens Industry, Oct. 1997, pp. 74–78.

Lee, Seungsin et al., "Antimicrobial and Blood Repellent Finishes for Cotton and Nonwoven Fabrics Based on Chitosan and Fluoropolymers," Textile Research Journal, 69(2), Feb. 1999, pp. 104–112.

Rahn, K. et al., "New Cellulosic Polymers By Subsequent Modification of 2,3–Dialdehyde Cellulose," Cellulose Chemistry and Technology, 32, 1998, pp. 173–183.

* cited by examiner

US 6,764,477 B1

CENTER-FILL ABSORBENT ARTICLE WITH REUSABLE FRAME MEMBER

BACKGROUND OF THE INVENTION

High-performance absorbent articles for feminine care and incontinence care tend to be too expensive for many peoples of the world. Disposable absorbent articles in less developed nations tend to be crude and much more prone to leakage than the more expensive articles available in more developed countries.

One long-elusive goal for high-performance articles is center fill, in which the absorbed fluid is predominantly retained in the center and is generally restrained from wicking to the sides of the article, from whence leakage may occur. Unfortunately, in traditional absorbent articles, there is generally no barrier to bulk flow or capillary wicking from the target region to the edges of the article, though several attempts have been proposed to reduce leakage and promote center fill. For example, fluid impervious cuffs and flaps have been widely used or proposed. These added barriers are costly and do not prevent fluid from reaching the edge of the absorbent article, though they can be effective in reducing leakage in some absorbent articles.

What is needed is a low-cost means of providing high-performance in sanitary napkins and related absorbent articles. What is needed further is an improved, low-cost means for promoting center fill and reducing flow toward the edges of the absorbent article for leakage reduction that offers improved feel and appearance of the article while also reducing leakage and reducing smearing of fluids across the surface of the article or other forms of failure.

SUMMARY OF THE INVENTION

A high-performance center-fill absorbent article such as a sanitary napkin has been invented comprising a reusable frame member which receives a smaller detachable and replaceable single-use absorbent device. The reusable frame member comprises a flexible, resilient outer shaping member which surrounds the single-use absorbent device and holds it in place against the body of the wearer for better body fit and flow control. The reusable frame member also can provide further leakage control through additional barriers to fluid flow, desirably through the use of a wicking barrier such as an impervious polymeric film on a portion of the body-side surface of the reusable frame member to prevent leakage from the sides of the single-use absorbent device. Desirably, the outer shaping member in the reusable frame has a central void for receiving the single-use absorbent device, with a wicking barrier lining the sides of the void and extending laterally outward therefrom to reside on the surface of the outer shaping member to prevent soiling of the outer shaping member by body fluid. Also desirably, the wicking barrier or other impervious film extends across the central void to define a liquid impervious sublayer which can prevent fluid from escaping the central void and/or provide a surface for holding the single-use absorbent device in the central void.

The single-use absorbent device is an inexpensive, disposable absorbent element such as a commercial ultrathin pad or pantiliner that is capable of receiving and holding a substantial quantity of fluid, and that can be discarded and replaced with a fresh single-use absorbent device. Thus, a composite sanitary napkin or incontinence device comprising a reusable frame and a replaceable single-use absorbent device offers an economical, high-performance article. A reusable frame comprising an outer shaping member combined with a single-use absorbent device provides leakage protection superior to that possible with the single-use absorbent device alone. The improved leakage protection is generally due to the enhanced body fit and flow containment offered by the reusable frame and by the center-fill geometry offered by the composite absorbent article.

The single-use absorbent devices suited for use with the reusable frame member desirably comprise a liquid pervious topsheet, a baffle layer connected to the topsheet, an absorbent core between the topsheet and the baffle layer, and attachment means for detachable connection to the reusable frame member such as adhesive material on the baffle layer and release paper over the adhesive material. The single-use absorbent device can be detachably connected to the reusable frame member once the release paper has been removed, exposing the adhesive on the single-use absorbent device. The single-use absorbent device can be placed within a central void within the outer shaping member of the surrounding reusable frame, which is the most preferred embodiment, or can lie substantially above the outer shaping member. After use, the single-use absorbent device can be removed from the reusable frame member and replaced with a new single-use absorbent device without always requiring disposal of the reusable frame member.

The reusable frame comprises an outer shaping member and means to prevent premature soiling of the outer shaping member such as at least one of a wicking barrier on the body-side surface of the outer shaping member or a hydrophobic surface on the outer shaping member, especially a surface that is unitary therewith. The reusable frame further comprises an impervious sublayer beneath the central void for holding the single-use absorbent device (e.g., by direct contact therewith or by supporting an additional layer of material above the impervious sublayer but beneath the central void) and/or for preventing fluid from escaping from the central void. The impervious sublayer may be directly visible through the central void when viewed from above body-side surface of the reusable frame member, or may be covered by another layer of material. The impervious sublayer may be integral with the wicking barrier, as is the case when the wicking barrier is a single polymeric film extending over the outer shaping member and across the central void, descending into the central void to maintain a void for receiving the single-use absorbent device. Alternatively, the impervious sublayer may be a part of a backsheet on the garment-side surface of the reusable frame member.

The outer shaping member, in some embodiments, is absorbent and can absorb body fluids, but this should only occur when the central absorbent member is substantially loaded with fluid. In other words, the outer shaping member may provide additional absorbent capacity to prevent leakage if that of the central absorbent member is exceeded, but under normal use the fluid is received by the central absorbent member and is hindered from wicking into an absorbent outer shaping member by virtue of a wicking barrier or hydrophobic treatment on the surface of the outer shaping member. But when fluid wicks to the longitudinal ends of the central absorbent member or other selected regions that are normally only wetted when the central absorbent member is highly loaded, the wicking barrier may be absent there or provided with apertures to enable fluid access to the outer shaping member.

The reusable frame and the outer shaping member generally have a size similar to known sizes for high-performance absorbent articles, being small enough to fit the user comfortably but large enough to receive a smaller single-use absorbent device such as a pantiliner. In particular, the reusable frame is wider than the single-use absorbent device.

In conventional sanitary napkins and other absorbent articles, the article can become excessively bunched or compressed when wetted because the material of the absorbent core collapses when wetted. In contrast, even when the outer shaping member of the present invention is cellulosic, by maintaining the outer shaping member in a dry state, it can maintain its shaping and body fit functions throughout use. Thus, the outer shaping member can serve as a shaping and body fit element as well as a "cradle" to hold the single-use absorbent device and the wicking barrier in place.

Hence, in one aspect, the present invention resides in a flexible, reusable frame member attachable to the undergarments of a wearer for receiving a suitable single-use absorbent device, the single-use absorbent device being detachably connectable to the reusable frame member, the reusable frame member comprising:

a) an outer shaping member comprising a layer of flexible material having a width greater than the width of the single-use absorbent device and comprising a central void therein for receiving at least a portion of the single-use absorbent device, wherein the outer shaping member is protected from premature soiling by at least one of a hydrophobic surface unitary to the outer shaping member and a wicking barrier attached to the body-side surface of the outer shaping member;

b) a liquid impervious sublayer attached to the outer shaping member and extending beneath at least a portion of the central void; and c) attachment means for attaching the outer shaping member to the undergarments of the wearer.

The attachment means may be adhesive deposited on the garment-side surface of the frame, or mechanical fasteners, or wings or tabs that wrap the sides of the garments to hold the frame in place, the wings or tabs preferably further comprising adhesive or mechanical fasteners such as VELCRO™-style hook material for attachment to the cloth of the panties.

The impervious sublayer can prevent of leakage of fluid form the central void and/or can define a surface that can adjoin the single-use absorbent device or be attached thereto. Desirably the impervious sublayer spans the width of the central void, but it need not completely cover the area beneath the central void. For example, in a less preferred embodiment, the impervious sublayer could have a central hole therein which could be covered and sealed by attachment of the surrounding impervious sublayer to an impervious baffle layer of a single-use absorbent device, thus preventing leakage of fluid.

In another aspect, the invention resides in a composite absorbent article comprising the above-mentioned reusable frame member and a single-use absorbent device detachably connected to the reusable frame member and disposed substantially over the central void of the reusable frame member.

In another aspect, the invention resides in a package comprising at least one reusable frame member, as previously described, and a plurality of single-use absorbent devices suitable for use with the reusable frame member, each single-use absorbent device comprising release paper disposed over the adhesive on the garment-side surface thereof. The package desirably contains printed indicia explaining the multi-use nature of the reusable frame member and how to use the single-use absorbent devices with the reusable frame member.

In yet another aspect, the invention resides in a composite absorbent article having a body side and a garment side, the composite absorbent article comprising:

a) an outer shaping member comprising a layer of a resilient material with a central void therein;

b) a liquid impervious wicking barrier disposed on the body-side surface of the outer shaping member;

c) a backsheet disposed on the garment-side surface of the outer shaping member;

d) a detachable single-use absorbent device disposed above the wicking barrier and contained at least partially within the central void of the outer shaping member; and e) attachment means to detachably connect the single-use absorbent device to the outer shaping member.

In yet another aspect, the invention resides in a method for improving at least one of the body fit and leakage protection of a single-use absorbent device for absorbing body exudates from the body of a wearer, comprising a) attaching a flexible, reusable frame member to the undergarments of the wearer, the frame member comprising an outer shaping member comprising a layer of flexible material having a width greater than the width of the single-use absorbent device, a liquid impervious web or film substantially covering one of the body-side surface and garment-side surface of the outer shaping member, and a central void for receiving at least a portion of the single-use absorbent device;

b) attaching the single-use absorbent device to the body-side surface of the frame member, such that a portion of the absorbent device extends into the central void of the outer shaping member.

In still another aspect, the invention resides in a method for economically providing protection of undergarments from exudates from the body of a wearer, comprising:

a) providing a fresh single-use absorbent device having a width and a garment-side surface, comprising a topsheet, a baffle layer attached to the topsheet, an absorbent core between the topsheet and the baffle layer, and adhesive on the baffle layer;

b) attaching a flexible, reusable frame member to the undergarments of the wearer, the frame member comprising an outer shaping member comprising a layer of flexible material having a width greater than the width of the single-use absorbent device, a liquid impervious web or film covering at least a portion of one of the body-side surface or garment-side surface of the outer shaping member, the outer shaping member having a central void for receiving at least a portion of the single-use absorbent device;

c) contacting the adhesive on the baffle layer of the fresh single-use absorbent device to the reusable frame member such that the single-use absorbent device is disposed over the central void and attached to the reusable frame member;

d) bringing the undergarments toward the body of the wearer such that the single-use absorbent device is in contact with the body of the wearer;

e) detaching the single-use absorbent device from the reusable frame member after a quantity of fluid has been absorbed by the single-use absorbent device, whereby the single-use absorbent device has become used;

f) discarding the used single-use absorbent device;

g) providing a fresh single-use absorbent device; and h) repeating steps (c) through (f).

The outer shaping member may be a section of foam, coform, airlaid web, fluff pulp, or other cellulosic material encased in a polymeric film or nonwoven web to maintain integrity and, in some embodiments, to maintain dryness of the outer shaping member. The outer shaping member, for example, can be a polyurethane foam; a polyethylene foam such as the product known as VOLARA™ 2a polyethylene foam, obtained from Voltek Corp., of Lawrence, Mass.; or a foam rubber material (e.g., foamed styrene butadiene), foamed silicones, or foamed vinyl plastic. Several such foams can be obtained from Woodbridge Foam Fabricating, Inc., located in Chattanooga, Tenn., from the E. N. Murray Company, Inc., located in Denver, Colo., and Astro-Valcour, Inc., located in Glens Falls, N.Y. Foam materials desirably have a density of about 0.02 grams per cubic centimeter (g/cc) to about 0.1 g/cc, and should have suitable flexibility for comfort and good shaping. The foam material can be treated to be absorbent and/or hydrophilic, but need not be hydrophilic.

In the case of a closed-cell foam or a foam with an impervious skin on the outer surface, the surface of the foam itself can serve as a wicking barrier having both a vertical component and a horizontal component on the body-side surface of the shaping member. Thus, in general, the outer shaping member can comprise an integral wicking barrier or can have an additional polymeric barrier provided on its surface, or can be separated from the single-use absorbent device by a separate layer of barrier material serving as a wicking barrier.

An outer shaping member comprising foam or other materials can be preshaped to conform suitably to the body. Examples of materials and methods for preparing conformable, resilient shaped members are disclosed in U.S. Pat. No. 5,591,150, issued Jan. 7, 1997 to Olsen et al. The outer shaping member can comprise absorbent materials, particularly cellulose, such as a regenerated cellulose foam or stabilized fluff pulp or air laid wood fibers, stabilized with thermoplastic fibers, crosslinkers, or wet strength agents, and may be preshaped or can be planar.

The outer shaping member can be a composite element, such as a layer of cellulosic fibers joined to a polymeric foam layer. In one embodiment, the outer shaping member is extensible such that its size can be adjusted for improved fit. The outer shaping member can also be biodegradable and/or flushable, if desired.

In a preferred embodiment, the outer shaping member comprises at least one layer of a low density, resilient nonwoven web with continuous fibers such as spunbond or meltblown or with staple length fibers such as bonded carded webs. In particular, highloft nonwoven webs can be used in creating an outer shaping member. R. Krema et al. also describe advances in highloft materials in the article "What's New in Highloft Production," Nonwovens Industry, Oct. 1997, pp. 74–78. Highloft materials are defined therein as "low density fiber network structures characterized by a high ratio of thickness to weight per unit area. The fibers may be continuous or discontinuous, bonded or unbonded. Highloft battings have no more than 10% solids, by volume, and are greater than 3 mm (0.13 inches) in thickness." Methods for forming such materials are discussed therein, including the folding of carded webs, airlaid webs, or needled felts by perpendicular lappers to create pleats and folds (perpendicular layers) that are bonded by through air thermal bonding or mechanical bonding. Useful perpendicular lappers include vibrating lappers and reciprocating combs. Materials so maid are sometimes termed "perpendicular laid webs." Exemplary materials are the "Struto" highloft nonwoven materials available from Georgia Textile Machinery, Dalton Georgia, and related materials developed at the University of Liberec in the Czech Republic, including those taught in the related European Patent 516964-B1 published Nov. 27, 1996, by R. Krema et al. The "Struto" materials include corrugated nonwovens of high thickness (e.g., over 2 mm, specifically over 4 mm and more specifically over 7 mm in thickness when measured at a load of 0.05 psi) that have been thermally bonded after being corrugated. Such structures can contain one or more natural fiber types (e.g., cotton or wool) and/or synthetic fiber types (polypropylene, polyethylene, polyester, nylon, polyvinyl alcohol, rayon, and the like).

Further examples of useful materials for production of an outer shaping member include highloft polyester nonwovens that have been spray adhesive bonded or needle punched (including materials commonly used for quilt batting, mattress padding, comforters, and the like, available in piece form or desirably as roll goods), bicomponent bonded carded webs or spunbonds or meltblowns, heavy weight microfiber homopolymer meltblown (e.g., webs over 100 gsm) or blends of natural and synthetic fibers such as through-air-bonded bicomponent polyolefins and rayon fibers in a carded web construction. In addition, nonwovens which are post-modified to achieve loft and bulk through processes such as corrugating or creping can also be used to form a resilient outer shaping member. Other exemplary creped and corrugated nonwoven webs of value in construction of outer shaping members according to the present invention are disclosed in U.S. Pat. No. 5,753,343, "Corrugated Nonwoven Webs of Polymeric Microfiber," issued May 19, 1998 to Braun et al.; U.S. Pat. No. 4,421,812, "Method of Making a Bonded Corrugated Nonwoven Fabric and Product Made Thereby," issued Dec. 20, 1983 to D. Plant; and WO 97/19808, "Creped Hydroentangled Nonwoven Laminate and Process for Making," by W. Jackson, publ. Jun. 5, 1997.

For best comfort, the outer shaping member or outer absorbent member desirably should be soft, resilient and easily compressible. The resiliency should be in the range of about 15 percent to about 60 percent rebound, preferably about 15 percent to about 50 percent and more preferably about 15 percent to about 35 percent, as determined by the ASTM Test Method D3574-91 procedure H. Compressibility should be in the range of about 0.69 kPa (0.1 pounds per square inch (psi)) to about 13.8 kPa (2 psi) at 50% compression, preferably from about 2.1 kPa (0.3 psi) to about 11.7 kPa (1.7 psi) at 50% compression and most preferably from about 3.45 kPa (0.5 psi) to about 10.3 kPa (1.5 psi) at 50% compression, as determined by the ASTM Test Method D3574-91 procedure C.

Generally, the outer shaping member has a thickness of at least about 1 mm, specifically at least about 2 mm, more specifically at least about 3 mm, and most specifically from about 3 mm to about 7 mm. Desirably, the average thickness of the shaping member is at least about 20 percent of the average thickness of the single-use absorbent device, and more specifically is at least about 30 percent of the average thickness of the single-use absorbent device. The thickness of the outer shaping member can also be greater than that of the single-use absorbent device. For example, the average thickness of the single-use absorbent device can lower by at least about 20 percent or at least about 50 percent than the average thickness of the outer shaping member.

The "edge width" of the outer shaping member, defined herein as the lateral distance along a continuous portion of the outer shaping member along the transverse centerline, specifically from the inner edge (adjacent the single-use absorbent device) of the outer shaping member to the outer edge thereof, is desirably at least about 2 mm and specifically at least about 3 mm, more specifically at least about 4 mm. For example, a 7 cm wide rectangular foam section with a 5 cm wide central depression therein for receiving a single-use absorbent device would have an edge width of 1 cm.

The outer shaping member may have any useful shape known in the art, including that of a rounded rectangle, a dog bone, an hourglass, an ellipse, and the like. In a preferred embodiment, the outer shaping member comprises a central void for receiving at least a part of a single-use absorbent device. The central void of the outer shaping member may be a hole passing completely through the outer shaping member, either contained within a unitary outer shaping member like a donut hole or dividing the outer shaping member into two halves. Alternatively, the central void can be a depression not devoid of material, but having a substantially lower thickness than the remainder of the outer shaping member.

The outer shaping member may surround the entire single-use absorbent device or only surround its longitudinal sides in the target zone (typically the crotch region) or other region where lateral leakage is likely. Alternatively, the single-use absorbent device may descend into a central void within the outer shaping member wherein the in-plane dimensions of the central void are smaller than the single-use absorbent device such that the longitudinal sides of the single-use absorbent device overlap the outer shaping member, forming an overlap region. When the outer shaping member comprises two sections separated by the central void, the two sections are held together by a web of material which can be the impervious sublayer (e.g., a portion of the backsheet or wicking barrier layer), or a topsheet or a nonwoven envelope around all or part of the outer shaping member.

For best results in achieving a center-fill effect for fluid containment with the help of a reusable outer shaping member, the single-use absorbent device should be at least partially isolated from the surrounding outer shaping member, such that fluid communication between the two members is hindered or prevented. Isolation means are desired beyond what is normally provided by the baffle layer of the replaceable single-use absorbent device (e.g., a typical commercial sanitary napkin). The isolation can be achieved with barrier material preferably spanning a vertical distance between the single-use absorbent device and the surrounding outer shaping member to interfere with wicking of fluid (or other forms of flow) from the center of the single-use absorbent device toward the edges of the composite article (the composite article comprising the combination of the single-use absorbent device and the reusable frame). The barrier material also desirably spans a horizontal distance on the surface of the composite article for reduced surface smearing of fluid, reduced leakage and improved control of fluid flow.

The wicking barrier desirably is a thin, flexible, liquid impervious material such as a film of polyethylene, polypropylene, latex, or other polymers. It can also be a tissue layer or other paper structure impregnated with hydrophobic matter or fluid-resistant sizing. It can also be a nonwoven web comprising hydrophobic fibers such as a meltblown layer or a substantially liquid impervious textile or paper material made from hydrophobic fibers. Selected portions of the wicking barrier may be apertured or rendered less hydrophobic than the bulk of the wicking barrier to provide limited regions where fluid communication between the single-use absorbent device and the outer shaping member is possible in the event that leakage from the single-use absorbent device occurs. For example, a vertical component of the wicking barrier lining the central void of the outer shaping member may be liquid impervious, while portions of the wicking barrier on the body-side surface of the outer shaping member away from the single-use absorbent device may be apertured to provide flow access to the underlying outer shaping member if fluid escapes from the single-use absorbent device.

Alternatively or in combination with wicking barriers of forms mentioned previously, the wicking barrier can also comprise a hydrophobic coating on the body-side surface of the outer shaping member or hydrophobic matter that impregnates the body-side surface of the outer absorbent member. Such coating and impregnates can include fluoropolymers, silicone compounds, polyolefin; waxes; phenolic resins or other resins which are cured after coating or impregnating the outer shaping member, and the like.

Alternatively, the outer shaping member may be inherently hydrophobic with a hydrophobic surface integral with the outer shaping member. Generally, no additional hydrophobic coating or wicking barrier is needed for a hydrophobic outer shaping member if the fluid-contacting surface is substantially non-porous (e.g., free of voids that can receive and retain menses or other fluids in substantial quantities that would require discarding the reusable frame member).

In another embodiment, the outer shaping member does not comprise a separate wicking barrier on its body side surface but does comprise a liquid impervious backsheet on its garment-side surface to prevent whatever fluid that might enter the outer shaping member from escaping to soil the garments of the wearer. In this embodiment, fluid containment in the single-use absorbent device and a center-fill effect is provided primarily by the geometry and shaping provided by the composite absorbent article and by whatever barrier to lateral flow is provided by the single-use absorbent device. The geometry of the composite absorbent article can include a gap between the longitudinal sides of the single-use absorbent device and the inner sides of the central void in the outer shaping member that receives the single-use absorbent device, thus reducing fluid communication to a degree. If the absorbent capacity of the single-use absorbent device is exceeded or if fluid begins to leave the edges of the single-use absorbent device, then the outer shaping member is readily available to receive fluid. In this case, the outer shaping member desirably comprises an absorbent foam or absorbent fibers such as fluff pulp. However, once the outer shaping member has absorbed a quantity of fluid, it will generally be necessary to discard the outer shaping member as well as the single-use absorbent device.

Typically, fluid reaches the edges of pantiliners and other single-use absorbent devices suitable for use in the present invention before the absorbent capacity of the single-use absorbent device has been reached, so without a wicking barrier, it is likely that the outer shaping member may be soiled with fluid earlier than would have been necessitated by the limited absorbent capacity of the single-use absorbent device, and it is likely that a wicking barrier to prevent lateral flow from the single-use absorbent device would have resulted in the fluid being contained within the single-use absorbent device without leakage and in more efficient use of the absorbent material in the single-use absorbent device. Thus, it is preferred that the outer shaping member comprise a wicking barrier on its body-side surface to better contain fluid within the single-use absorbent device, though the outer shaping member can still be absorbent and have a limited degree of fluid communication with the single-use absorbent device to provide a secondary source of absorbent material in the event that the capacity of the single-use absorbent device is exceeded.

The single-use absorbent device desirably comprises a baffle layer attached to the garment-side surface thereof. The baffle layer may be identical to or comprise a part of the wicking barrier that shields the outer shaping member from fluid. Thus, a baffle attached to the single-use absorbent device may be substantially larger in dimensions than the single-use absorbent device to permit it to form a ledge on the body-side surface of the outer shaping member surrounding the single-use absorbent device. The baffle then should be adhesively or thermally attached to the single-use absorbent device, but detachably connectable to the outer shaping member, such as by mechanical attachment means or detachable adhesive means. Adhesive means can include pressure sensitive adhesives that can be adhered and detached from a surface multiple times. Mechanical means can include, for example, a hook and loop attachment such as Velcro®, snaps, tabs that fit into narrow slots to engage an object, material in the outer shaping member that forms pockets or lips between the outer shaping member and the backsheet for receiving a single-use absorbent device restrained by overlapping peripheral lips in the outer shaping member, magnetic attraction, inelastic straps or elastic straps passing over the longitudinal ends of the single-use absorbent device, and the like. Fiber entanglement can also serve as a mechanical fastening means, wherein fibers on one surface become entangle with fibers on an adjacent surface to join the two surfaces, as described more fully in U.S. Pat. No. 5,910,137, issued Jun. 8, 1999 to Clark et al. In the embodiment using peripheral lips, the lips are formed by a layer of material within the outer shaping member having margins abutting the longitudinal sides of the central void, wherein the margins can be lifted away from the plane of the reusable frame member to form pockets for receiving the longitudinal sides of the single-use absorbent device.

The topsheet of the single-use absorbent device desirably covers substantially only the single-use absorbent device, but may extend to the outer shaping member also, though the body-contacting portions of the outer shaping member preferably are covered with a soft topsheet material such as a nonwoven web that needs not be liquid pervious.

The reusable frame member may be provided in a package with a plurality of single-use absorbent devices or sold separately, preferably with packaging indicia linking the reusable frame member to particular single-use absorbent devices best suited for use therewith. By way of example, the package may comprise a paperboard carton or an outer flexible polymeric wrap, and desirably has printed indicia thereon indicating the multiple use capability of the reusable frame member. A package containing one or more reusable frame members and a plurality of single-use absorbent devices desirably is suitable for placement on shelves in a retail outlet and desirably has a rectilinear geometry or other shape suitable for stacking.

Desirably, the interaction of the reusable frame member with the single-use absorbent device while in use against the body of the wearer results in favorable deformation or folding of the article to provide a W-shape of the composite absorbent article, the composite absorbent article comprising the reusable frame member attached to the single-use absorbent device. In particular, the reusable frame member has longitudinal sides capable of folding upward during lateral compression, representing the outer arms of a W-shape, while the single-use absorbent device is urged to deflect vertically upwards along the longitudinal centerline, representing the upwardly flexed central mound (such as an inverted-V shape or inverted-U shape) of the generally W-shaped composite absorbent article. The longitudinal sides of the central void help promote W-shape folding of the composite absorbent article during lateral compression in use, but shaping is even further controlled to represent a desirable W-shape if the composite absorbent article further comprises a central rising member (hereafter described) disposed below the single-use absorbent device.

BRIEF DESCRIPTION OF THE DRAWINGS

FIGS. 5A and 5B depict cross-sections of a composite absorbent article according to the present invention comprising a central rising member for improved body-fit when exposed to lateral compression in use, wherein FIG. 5A depicts the composite absorbent article prior to lateral compression and FIG. 5B depicts the composite absorbent article after lateral compression.

DETAILED DESCRIPTION OF THE DRAWINGS

Figure 1A:
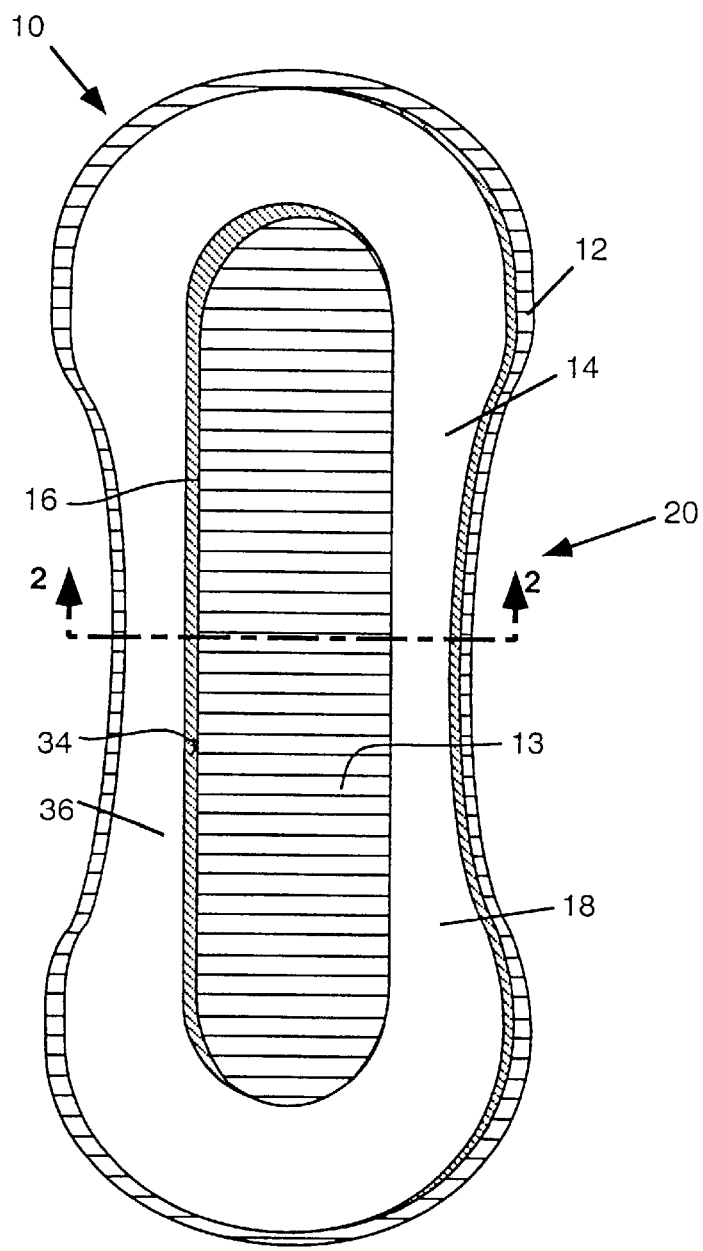
FIGS. 1A and 1B depict a top view of a reusable frame member and an associated single-use absorbent device, respectively.
Figure 1B:
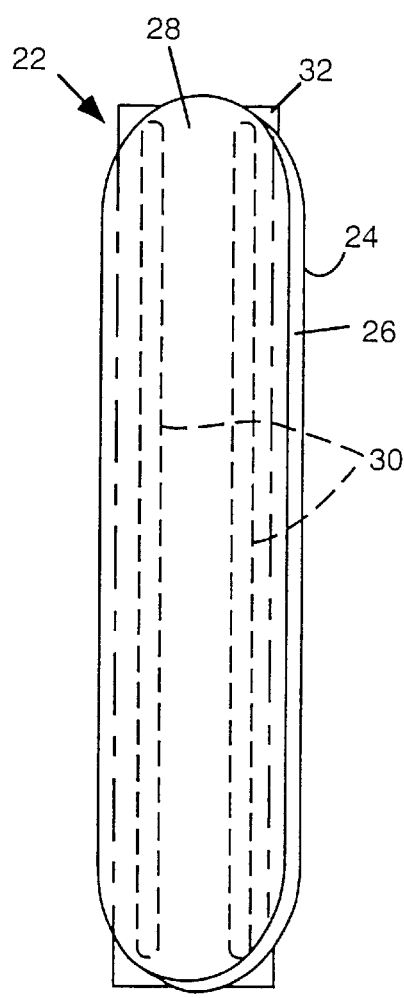

FIGS. 1A and 1B depict a top view of a reusable frame member 10 (FIG. 1A) suitable for attachment to undergarments such as panties and for receiving a smaller single-use absorbent device 22 (FIG. 1B). The reusable frame member 10 comprises a backsheet 12, which may be optional in some embodiments, an outer shaping member 14 having a central void 16 therein, the central void 16 in the outer shaping member 14 having a length substantially greater than its width and having a size and shape suitable for receiving all or part of a single-use absorbent device 22, and a wicking barrier 18 disposed over the body-side surface of the outer shaping member 14. In this embodiment, the portion of the backsheet 12 beneath the central void 16 serves as an impervious sublayer 13 beneath the central void 16 which provides a surface for attachment of the single-use absorbent device 22 and prevents escape of fluid from the central void 16.

The single-use absorbent device 22 comprises a baffle layer 24, an absorbent core 26, a topsheet 28, adhesive bands 30 on the garment-side surface of the baffle layer 24, and release paper 32 protecting the adhesive bands 30 until the single-use absorbent device 22 is ready for attachment to the reusable frame 10. The release paper 32 is removed prior to placing the single-use absorbent device 22 over the central void 16 of the reusable frame member 10.

The absorbent core 26 of the single-use absorbent device 22 can comprise any absorbent material known in the art, but for economic reasons, low cost materials are preferred such as fluff pulp, peat moss, coform, airlaid webs, joined layers of absorbent tissue, and the like. The baffle layer 24 and topsheet 28 can likewise be any useful materials known in the art such as nonwoven webs for the topsheet 28 and polyolefin films for the baffle layer 24.

In saying that the central void 16 can receive part of a single-use absorbent device 22, it is preferred that the plan-view area of the central void 16 be about 60% or greater of the plan-view area of the single-use absorbent device 22 (after removal of the release paper 32), more specifically about 70% or greater, and most specifically about 80% or greater. In a preferred embodiment, the plan-view area of the central void 16 is larger than that of the single-use absorbent device 22 at least due to a relatively greater width in the central void 16. The width of the central void 16 can exceed that of the intended single-use absorbent device 22 by at least about 5%, more specifically about 10% or greater, and most specifically from about 8% to about 25%. The single-use absorbent device 22 should be substantially more narrow than the outer shaping member 14 in the crotch region 20 such that the outer shaping member 14 surrounds the single-use absorbent device 22 in the crotch region 20. Desirably, the single-use absorbent device 22 is no wider than the central void 16 in the crotch region 20 or target region of the reusable frame member 10.

The wicking barrier 18 spans a vertical distance along the inner wall of the central void 16, thus defining a vertical component 34 of the wicking barrier 18. It also covers the body-side surface of the outer shaping member 14, thus defining a horizontal component 36 of the wicking barrier 18. The vertical component 34 of the wicking barrier spans a vertical distance that can be about 20 percent or greater of the average thickness of the single-use absorbent device 22, more specifically of about 50 percent or greater, more specifically still from about 60 percent to about 100 percent, and most specifically about 100 percent or greater of the average thickness of the single-use absorbent device 22. The vertical component 34 of the wicking barrier 18 can span a vertical distance of about 1 mm or greater, more specifically about 2 mm or greater, and most specifically about 3 mm or greater. As depicted in FIG. 1A, the horizontal component 36 of the wicking barrier 18 spans substantially all of the body-side surface of the outer shaping member 14, though it could span a lesser fraction thereof such as from about 25% to 90%, or from about 40% to about 80%, or about 50% or greater of the surface area of the outer shaping member 14.

In FIG. 1A, the backsheet 12 is exposed in the central void 16 of the reusable frame member 10. Thus, the impervious sublayer 13 is viewable from above the body-side surface of the reusable frame member 10 prior to use. In an alternate embodiment that is not shown, the wicking barrier 18 could extend across the central void 16, in contact with the underlying backsheet 12 or replacing the backsheet 12 under the central void 16, and thereby form the impervious sublayer 13.

The outer shaping member 14 can comprise a wide variety of flexible, resilient materials suitable for being worn against the body and for providing shape to a composite absorbent article comprising the reusable frame member 10 joined to the single-use absorbent device 22. Suitable materials can include polyurethane foams, foam rubber, and other foams; cellulosic webs such as fluff pulp or airlaid webs, including airlaid webs having a portion of thermoplastic fibers wherein the web is stabilized by thermal bonding; nonwoven webs, including high-loft bonded carded webs; wool; cotton; and the like.

The backsheet 12 of the reusable frame member can be any material known in the art, and desirably is a soft, liquid impervious material that can also be breathable.

Figure 2:
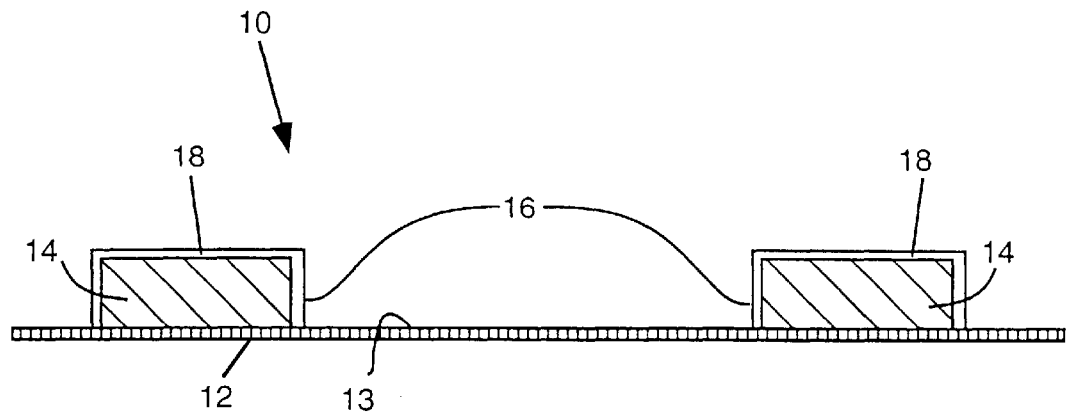
FIG. 2 is a cross-section taken from the reusable frame member depicted in FIG. 1A.

FIG. 2 shows a cross-section of the reusable frame member 10 of FIG. 1A taken along the transverse centerline. Here, the central portion of the backsheet 12 serves as the impervious sublayer 13 beneath the central void 16. The wicking barrier 18 covers the body-side surface of the outer shaping member 14 and covers the outer longitudinal sides of the outer shaping member 14 as well as the inner walls of the central void 16. A wicking barrier 18 or equivalent hydrophobic or impervious means on the inner walls of the central void 16 to prevent fluid communication from the single-use absorbent device 22 with the outer shaping member 14 is generally desired, especially when the outer shaping member 14 comprises absorbent materials such as fluff pulp or airlaid webs. A wicking barrier 18 on the outer, longitudinal sides of the outer shaping member 14 is less important but still useful. In a related embodiment not shown, the wicking barrier 18 may be formed from extensions of the backsheet 12 which wrap the outer shaping member 14.

Figure 3:
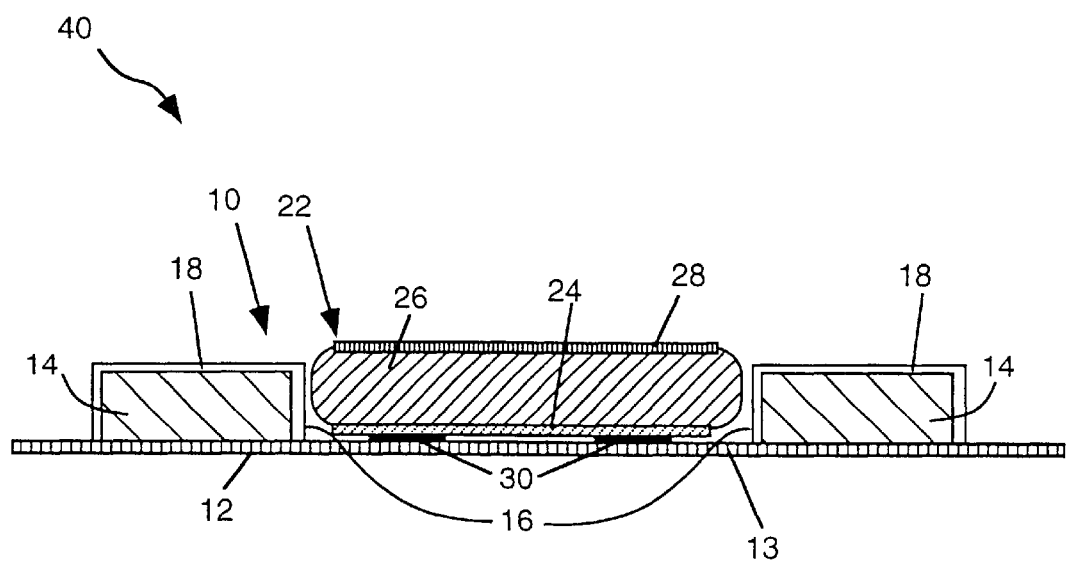
FIG. 3 is a modified version of FIG. 2 showing the presence of an added single-use absorbent device in the central void of the reusable frame member.

FIG. 3 depicts the transverse cross-section of a composite absorbent article 40 comprising the reusable frame member 10 of FIGS. 1A and 2 and a single-use absorbent device 22 attached to the reusable frame member 10, disposed within the central void 16 thereof. The single-use absorbent device 22 comprises an absorbent core 22, a baffle layer 24 with adhesive 30 thereon for attachment to the a backsheet 12 of the reusable frame member 10 within the central void 16, and an optional topsheet 28 which, in a related embodiment not shown, may wrap the longitudinal sides of the single-use absorbent device 22 or be joined to the baffle layer 24. Desirably, the single-use absorbent device 22 is a thin, inexpensive product such as a pantiliner or ultrathin pad, preferably without wings or tabs projecting from the longitudinal sides thereof. The baffle layer 24 is actually not needed when the reusable frame member has a backsheet 12 or central portion (not shown) of a wicking barrier 18 extending fully across the central void 16 serving as an impervious sublayer, and thus single-use absorbent devices 22 without a baffle layer 24 but merely comprising adhesive 30 on the garment-side surface of the absorbent core 26 can be used. (Release paper, not shown, would normally be attached over the adhesive sections prior to use.)

For commercial purposes, it is desirable to provide a plurality of low-cost single-use absorbent devices 22 without baffle layers in a package comprising a lesser number of reusable frame members 10, or to sell low-cost single-use absorbent devices 22 in package marked with indicia linking it to a package containing one or more reusable frame members 10, the intent being that each reusable frame member 10 could be used with a plurality of single-use absorbent devices 22 that are each attached to the reusable frame member 10, used for liquid intake, then detached from the reusable frame member 10 and replaced with a fresh single-use absorbent device 22 to form the composite absorbent article 40 useful for absorbing fluids from the body of a wearer.

The backsheet 12 or other surface for contacting the adhesive 30 of the single-use absorbent device 22 must be strong enough to withstand the peel and tension forces of removing an adhesively attached single-use absorbent device 22 from the reusable frame member 10.

Figure 4A:
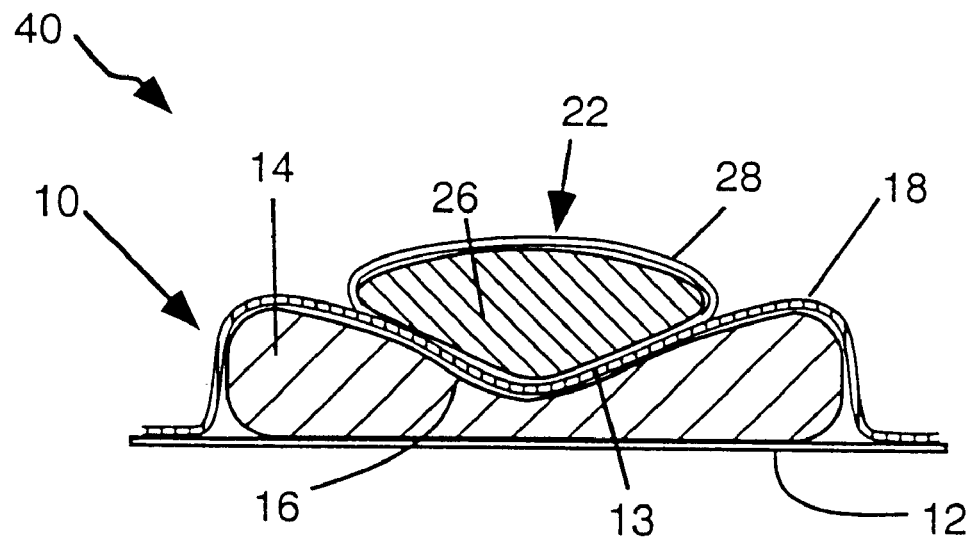
FIGS. 4A and 4B depict cross-sections of two versions of a composite absorbent article comprising a single-use absorbent device that overlaps with a portion of the outer shaping member outside the central void or depression therein.
Figure 4B:
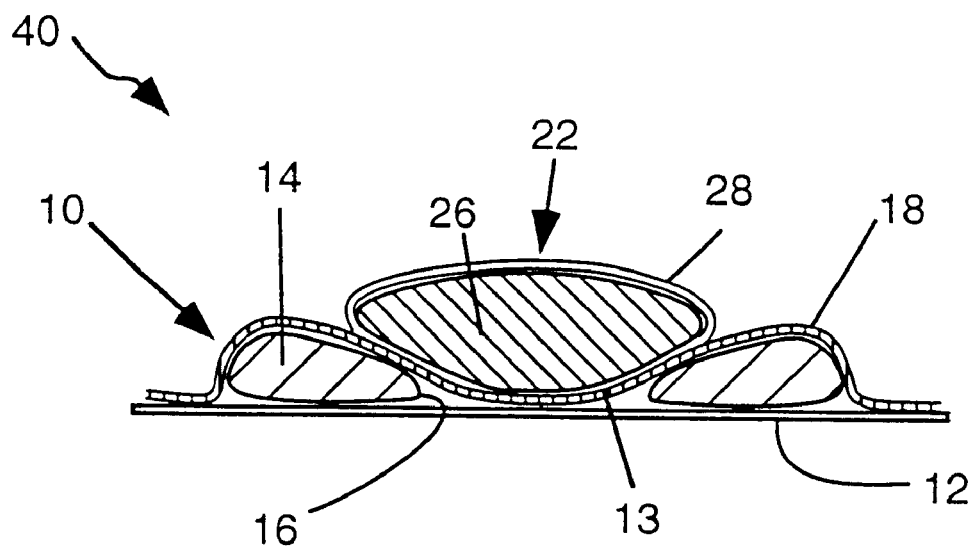

FIGS. 4A and 4B depict the transverse cross-sections of two versions of a composite absorbent article 40 comprising a reusable frame member 10 with a single-use absorbent device 82 (or detachable single-use absorbent device) attached. FIGS. 4A and 4B illustrate how a single-use absorbent device 22 can overlap with the sides of a central void 16 within an outer shaping member 14 in the reusable frame member 10, and shows how the sides of the central void 16 need not be vertical but do span a vertical distance, and further shows that the outer shaping member 14 can be contiguous (FIG. 4A) or discontiguous (FIG. 4B) across a transverse cross-section in general or across the transverse centerline.

In FIG. 4A, the single-use absorbent device 22 comprises an absorbent core 26 and a liquid pervious topsheet 28. The single-use absorbent device 22 is adhesively attached over the central void 16 of the outer shaping member 14, which is covered with a wicking barrier 18 and is backed by a backsheet 12 that is attached to the wicking barrier 18. In this embodiment, the wicking barrier 18 also forms the impervious sublayer 13 beneath the central void 16. Attachment means (not shown) join the single-use absorbent device 22 to the reusable frame member 10. The attachment means can include an adhesive coated baffle layer (not shown) on the garment-side surface of the single-use absorbent device 22, adhesive on the body-side surface of the wicking barrier 18 over the central void 16, hook and loop or other mechanical fastening means joining the facing surfaces of the reusable frame member 10 and the single-use absorbent device 22, or other means known in the art.

FIG. 4B follows FIG. 4A except that the outer shaping member 22 is now discontiguous, being split into two portions along the transverse cross-section shown. The gap between the two portions of the outer shaping member 22 defines the central void 16. Thus, the central void 16 is hole that passes completely through the outer shaping member 22, unlike the central void 16 in FIG. 4A, which is a depression.

While the overlap between the single-use absorbent device 22 and the reusable frame member 10 outside of the central void 16 may surrender a degree of containment of the sides of the single-use absorbent device 22 made possible by the walls of the central void 16 on other embodiments, a degree of overlap can be useful in providing good body-fit in use when the composite absorbent article 40 experiences lateral compression. The overlapping regions provide a degree of resiliency to the article when laterally compressed, allowing a W-shaped article under lateral compression to spring back to a substantially flat article when not laterally compressed potentially for improved comfort and appearance of the article.

Figure 5A:
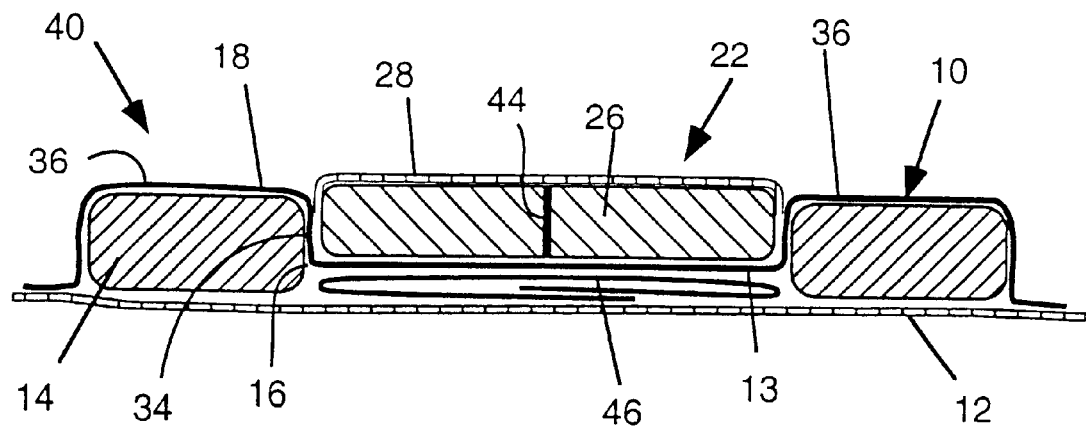
Figure 5B:
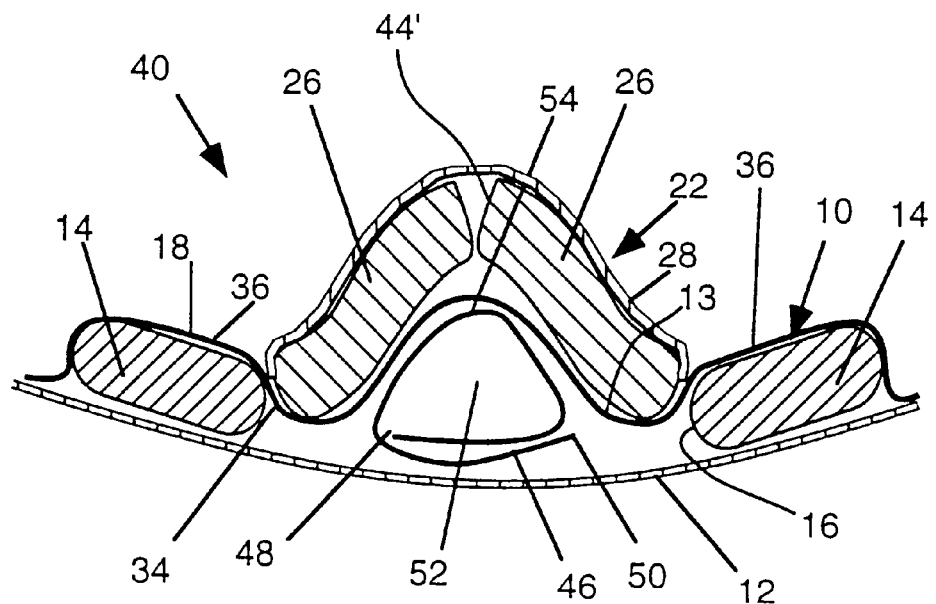

FIGS. 5A and 5B depict cross-sections of an embodiment of a composite absorbent article 40 according to the present invention useful as a sanitary napkin, incontinence pad, or other article for absorbing body exudates. The cross-section is taken near the longitudinal center of the article 40 in the transverse direction (e.g., along the transverse centerline). In FIG. 5A, the composite absorbent article 40 comprises a reusable frame member 10 comprising a wicking barrier 18, a liquid impervious backsheet 12 desirably attached to the wicking barrier 18, and a resilient outer shaping member 14 between the wicking barrier 18 and the backsheet 12. The outer shaping member 14 may comprise two longitudinal strips of material or comprise a unitary layer of resilient material such as coform or a densified airlaid web with a rectangular or oval hole therein. In any case, the internal walls of the outer shaping member 14 define a central void 16. The impervious sublayer 13 beneath the central void 16 comprises a central portion of the wicking barrier 18, although in an embodiment that is not shown, the wicking barrier 18 could be apertured for controlled release of fluid, in which case the backsheet 12 would serve as the impervious sublayer 13.

The central void 16 is suited to receive a single-use absorbent device 22 which can be entirely contained within the central void 16, as depicted, or the single-use absorbent device 22 can be somewhat wider than the central void 16 such that the single-use absorbent device 22 overlaps (not shown) a portion of the outer shaping member 14. Generally for best leakage control, it is desirable to have the single-use absorbent device 22 sized to fit substantially within the central void 16 of the reusable frame member 10.

The single-use absorbent device 22 can be provided with a longitudinal shaping line 44, which enables the upward folding of the absorbent core 26 during lateral compression. The single-use absorbent device 22 may further be provided with a baffle layer (not shown) on the garment-side surface and with adhesive thereon (not shown).

The absorbent core 26 is separated from the outer absorbent member 14 by the wicking barrier 18. In the embodiment shown, the wicking barrier 18 passes beneath the absorbent core 26 and has a vertical component 34 extending vertically along the walls of the central void 16 and further extends horizontally over the body-side surface of the outer absorbent member 14 to define a horizontal component 36 or ledge on the surface of the outer absorbent member 14.

The wicking barrier 18 can comprise an impermeable, flexible polymeric film, a meltblown film, an apertured film, a hydrophobically treated tissue, a nonwoven web, or other wicking inhibiting layer, or a hydrophobic coating on the outer shaping member 14. The wicking barrier 18 serves to prevent lateral flow from the sides of the single-use absorbent device 22 to the outer absorbent member 14, which may be absorbent and porous, or to the longitudinal sides of the composite absorbent article 40.

Beneath the single-use absorbent device 22, as depicted in the embodiment of FIG. 5A, is a central rising member 46, depicted here as a section of folded flexible material capable of deflecting upwards when compressed from the sides. In this embodiment, the material is folded like the shape of the letter "e", though other configurations are also possible (e.g., flattened tubes, "W"-shaped cross-sections of resilient material, and the like). In the embodiment shown, the central rising member 46 is below the wicking barrier 18, which is generally preferred, but it may also be above the wicking barrier 18. In other embodiments, the central rising member 46 may reside within the single-use absorbent device 22 or may be attached to its garment-side surface.

The composite absorbent article 40 of FIG. 5A is depicted after lateral compression in FIG. 5B, where the central rising member 46 has deflected upward to urge the overlying single-use absorbent device 22 toward the body of the wearer. The ends 48, 50 of the central rising member 46 have moved toward the opposing longitudinal sides thereof as the upper portion 54 has buckled upward, resulting in formation of a void space 52 beneath the absorbent core 26 and specifically within the central rising member 46, though void space could also be created underneath a portion of the central rising member 46 during lateral compression as well for other types of central rising member. At least in the crotch region, the absorbent core 26 is not in direct fluid communication with the outer absorbent member 14 by virtue of the wicking barrier 18, and particularly the vertical component 34 which prevents fluid flow from the neighboring portions of the absorbent core 26 and the outer absorbent member 14. The horizontal component 36 of the wicking barrier on the surface of the outer absorbent member 14 also prevents fluid communication and surface smearing when the pad is momentarily severely deformed or compressed during the dynamic conditions of actual use. Therefore, the outer absorbent member 14 tends to remain dry even when the composite absorbent article 40 is wetted, and can therefore serve to control the shape and fit of the article 40 even if made of a material that would otherwise collapse when wet, thus maintaining good body contact and comfort even when the absorbent core 26 is substantially wet.

Figure 6A:
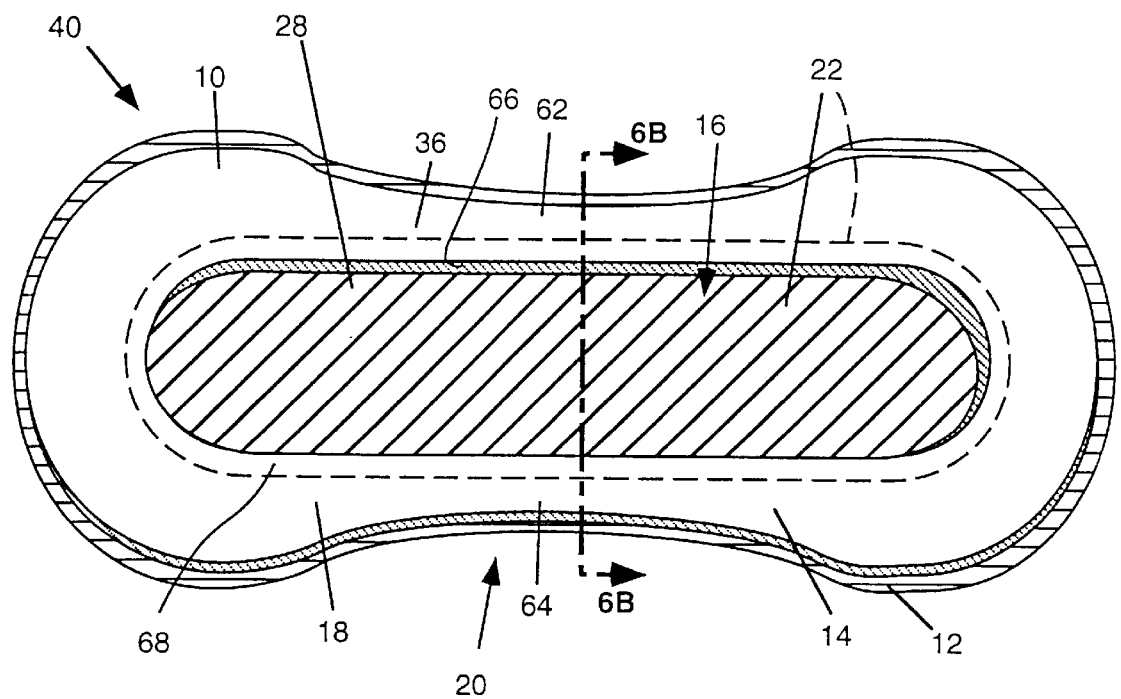
FIGS. 6A and 6B depict a top view and a transverse cross-section, respectively, of a composite absorbent article with peripheral lips for mechanically holding the single-use absorbent device in place.
Figure 6B:
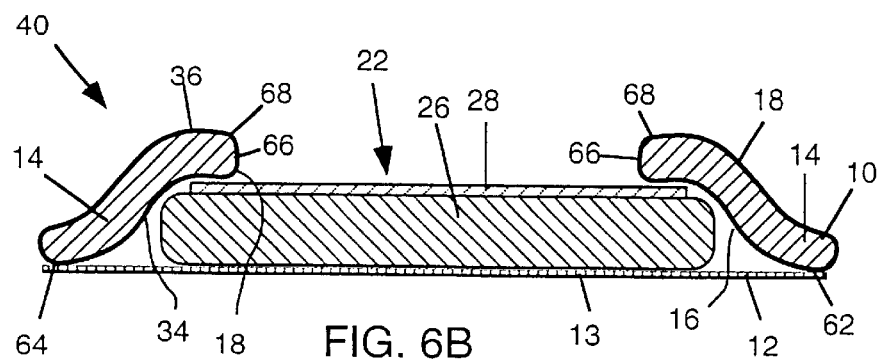

FIGS. 6A and 6B depict a composite absorbent article 40 comprising a reusable frame member 10 and a single-use absorbent device 22, in which the attachment means is mechanical. Specifically, the outer shaping member 14, which is substantially covered with a wicking barrier 18, is attached to the backsheet 12 at the transversely outward sides 62, 64 of the outer shaping member 14 but not near the interior walls 66 of the outer shaping member 14, such that the transversely inward portions thereof are unattached to the backsheet 12 and remain free to form peripheral lips 68 under which the single-use absorbent device 22 can be inserted into the central void 18. The lips 68 overlap the single-use absorbent device 22 and restrain it in the reusable frame member 10. Further attachment means (not shown) may be present, including adhesive, hook and loop elements, and the like. Optionally, the outer shaping member 14 need not be covered with a wicking barrier 18 but could be protected from premature soiling by a hydrophobic coating or by use of non-porous hydrophobic material for the outer shaping member 14.

As depicted, the peripheral lips 68 overlap the entire single-use absorbent device 22, but in alternative embodiments the peripheral lips 68 could only overlap the single-use absorbent device 22 along its longitudinal sides or along a portion of the longitudinal sides thereof. For ease of removal, one longitudinal end of the single-use absorbent device 22 could be free of overlapping peripheral lips 68 while the opposing longitudinal end could be inserted beneath the peripheral lips 68.

In the embodiment as depicted, the outer shaping member 14 should comprise a flexible material with sufficient stiffness to suitably restrain the single-use absorbent device 22 such that it will not detach from the reusable frame member 10 in use. The size of the lips 68 should also be optimized for the material selected to provide adequate restraining ability without significant difficulty in inserting the single-use absorbent device 22 or without discomfort caused by the thickness and width of the lips 68.

Other Configurations and Additional Components

The reusable frames and composite absorbent articles of the present invention can be combined with other functional materials internally (as by adding material into the absorbent material or on the barrier material) or externally (as by joining with additional layers), including but not limited to odor absorbents, activated carbon fibers and particles, baby powder, zeolites, perfumes, fire retardants, superabsorbent particles, nonwoven materials, plastic films or apertured films, extruded webs, closed cell foams, adhesive strips and tapes, tissue webs, electronic devices such as alarms indicating wetness or leakage and other wetness indicators, opacifiers, fillers, aerogels, sizing agents, antimicrobial agents, enzymes, ion exchange material, or enzyme inhibitors such as urease inhibitors to prevent the production of ammonia.

The reusable frames and composite absorbent articles of the present invention can also be adapted to form diapers, bed pads, incontinence articles, and other absorbent articles. Several useful diaper configurations which can be adapted according to the present invention to serve as a composite absorbent article with a reusable frame member and replaceable single-use absorbent device are described generally in U.S. Pat. No. 3,860,003 issued to Buell on Jan. 14, 1975 and U.S. Pat. No. 5,151,092 issued to Buell on Sep. 29, 1992.

Means can also be applied to reduce the tendency of a composite absorbent article to bunch or fold over onto itself during transverse compression. Wings, flaps, or tabs extending from the reusable frame member in the crotch region can fold over the edge of undergarments of the wearer to provide better fit, stability, and leakage protection, and can reduce undesirable bunching of the article. Wings and related structures are taught in the U.S. Pat. No. 5,267,992, "Shaped Sanitary Napkin with Flaps," issued to K. J. Van Tilburg, Dec. 7, 1993.; U.S. Pat. No. 4,687,478, "Shaped Sanitary Napkin with Flaps," issued to Van Tilburg, Aug. 18, 1987; U.S. Pat. No. 4,589,876, "Sanitary Napkin," issued to K. J. Van Tilburg, May 20, 1986; U.S. Pat. No. 4,285,343, "Sanitary Napkin," issued to R. M. McNair, Aug. 25, 1981.; U.S. Pat. No. 4,608,047, "Sanitary Napkin attachment Means," issued to W. B. Mattingly, Aug. 26, 1986; U.S. Pat. No. 5,342,342, "Disposable Diapers," issued to Kitaoka Aug. 30, 1994; and World Patent Application 99/00093 "Absorbent Article with Multi-Layered Extensible Wings," R. W. Patterson et al., Jan. 7, 1999.

The article may further comprise other leakage dams, cuffs, wings, pouches, elastic barriers, and other elements known in the art. Examples of useful cuffs and flow dams for reduced leakage are disclosed in U.S. Pat. No. 5,575,785, "Absorbent Article Including Liquid Containment Beams and Leakage Barriers," issued Nov. 19, 1996 to Gryskiewicz et al.

EXAMPLES

Examples of an absorbent article according to the present invention was made with the materials listed in Table 1 below:

TABLE 1

Basic materials used in construction of absorbent articles for the Examples.

| Component | Manufacturer | Description |
|---|---|---|
| Topsheet | | |
| Spunbond material | Kimberly-Clark Corp. | 0.6 osy polypropylene spunbond web, "Delta" version, treated with 0.3% add-on of surfactant (described below) |

TABLE 1-continued

Basic materials used in construction of absorbent articles for the Examples.

| Component | Manufacturer | Description |
| --- | --- | --- |
| Surfactant treatment | ICI Americas, Inc. | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less. |
| Fluff | Kimberly-Clark Corp. | Coosa River CR56 debonded softwood pulp comminuted with a hammermill |
| Densified airlaid webs | | |
| Completed web | Concert Fabrication, Ltee | 90% softwood fibers and 10% binder fibers with overall densities of 0.1–0.2 g/cc. |
| Fibers | Weyerhaeuser Co. | NB-416: bleached southern softwood kraft |
| Binder fibers | Hoechst Celanese Corp. (Trevira Company) | Celbond #255: PET core, activated co-polyethylene sheath, 50/50 core/sheath ratio, concentric, 2.8 dpf, with T-255 fiber finish |
| Impervious wicking barrier | | |
| Polyolefin film, colored | Edison Plastics Co. | A low density polyethylene, 20 gsm, rose color, 1 mil initially, 2 mil gauge after embossed with pattern MFST (male fine square taffeta), contact adhesive on one side |
| Polyolefin film, white | | Low density polyethylene, 18 gsm, opaque with added white pigment, about 1 mil |
| Pervious wicking barrier | | |
| Spunbond web | Kimberly-Clark Corp | 0.8 osy 2.7 denier, rose color, no surfactant |
| Backsheet | | |
| Polyolefin film | Edison Plastics Co. | A low density polyethylene, 20 gsm, rose color, 2 mil gauge after embossed with pattern MFST (male fine square taffeta), coated with contact adhesive on one side |
| Adhesive | National Starch and Chemical Co. | NS-34-5610, less than 15 gsm added, slot-coated, pinstripe pattern |
| Garment adhesive | National Starch and Chemical Co. | NS-34-5602, less than 45 gsm applied, slot coated, two 15 mm side lines of adhesive with a 19 mm space between them |
| Release paper | Akrosil Inc. | White base sheet, one side coated with silicone release agent, other side printed |

Example 1

Example 1 was made with a reusable frame member similar to that depicted in FIG. 1, but with a wicking barrier disposed over the entire surface of the outer shaping member and over the central void. The outer shaping member was made from a densified airlaid web having a basis weight of 175 gsm. The outer shaping member was cut to a dumbbell shape with a length of about 21.5 cm and a width at the transverse centerline of about 6 cm. A central portion of the outer absorbent member was removed by a die cutting operation to provide a central void in the outer absorbent member 18.7 cm long and 3.7 cm wide. The dumbbell-shaped outer absorbent member was placed on a backsheet (as described in Table 1) comprising a polymer film provided with contact adhesive. The entire surface of the outer shaping member was covered with a pink poly film, the same as the backsheet but with the adhesive side down, thus sealing the outer shaping member between two polymer films.

A commercial KOTEX® pantiliner was placed over the central void of the reusable frame member after the release paper was removed. The single-use absorbent device (the pantiliner) was then adhesively attached to plastic film in the central void, being substantially aligned longitudinal with the reusable frame member.

The pantiliner could be easily detached and reattached to the central void of the reusable frame member, providing a composite absorbent article with a sealed, reusable outer shaping member and a low-cost single-use absorbent device that could be readily detached and replaced with a fresh single-use absorbent device.

Example 2

Example 2 was made according to FIGS. 6A and 6B with dimensions substantially according to Example 1. Flexible Meltallecene polyethylene foam 1-mm in thickness having adhesive on one surface was stacked into a three-layer assembly, 3-mm in thickness, and cut to have a dog bone shape with a length of 225 mm and midpoint width of 64 mm. A central void in the form of a hole was cut in the dog bone-shaped foam material to have a rounded rectangular shape with a width of 43 mm and a length of 187 mm. The resulting foam layer with a central void served as the outer shaping member.

Tissue cut to the same outer shape as the foam of the outer shaping member, but without a central hole therein, was trimmed to make it about 5 mm narrower. The tissue was placed over exposed adhesive on the upper surface of a 1-mil thick rose-colored polyethylene backsheet layer, with the unexposed adhesive on the other side being covered by release paper. The outer shaping member was then placed over the tissue such that the tissue was centrally aligned and centered with respect to the outer shaping member. The tissue attached to the backsheet prevented the adhesive from attaching to the outer shaping member where the tissue was present, but still allow about 2.5 mm of exposed adhesive underneath the outer longitudinal sides of the outer shaping member to be free to attach to the backsheet. Thus, only the transversely outward portions of the outer shaping member were attached to the backsheet, with the inward portions being free to define lips for receiving a single-use absorbent device wider than the central hole cut into the outer shaping member.

The body-side surface of the foam outer shaping member was covered with a polyethylene film that extended to attach to the underlying backsheet at a periphery just outside the edges of the outer shaping member to help hold the outer shaping member in place and to prevent soiling of the body-side surface, though the hydrophobic closed-cell foam probably did not require a wicking barrier to prevent premature soiling. The film had a central hole in it substantially the same shape as the central void of the outer shaping member, but the hole was about 2 mm wider in the polyethylene film.

The combination of the backsheet covered in part with a tissue layer, the outer shaping member adhered to the backsheet, and the polyethylene film on the outer shaping member formed a reusable frame member. The central portion of the backsheet formed the impervious sublayer, which was not fully visible through the central void due to the presence of the tissue layer.

The single-use absorbent device comprised a layer of coform (70% bleached softwood fibers, 30% polypropylene) with a basis weight of 175 gsm cut to a rounded rectangular shape 54 mm wide by 201 mm long. The single-use absorbent device comprises a layer of spunbond topsheet material on the body-side surface and a layer of white 20 gsm polyethylene film as a baffle layer on the garment-side surface thereof. The single-use absorbent device could readily be fit under the peripheral lips of the reusable frame member and readily removed.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:

a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and b) a liquid impervious sublayer attached to the outer shaping member and extending beneath at least a portion of the central void, wherein the impervious sublayer is integral with the wicking barrier, wherein the wicking barrier extends beneath the entire central void and wherein the impervious sublayer comprises a central portion of the wicking barrier.

2. The reusable frame member of claim 1, wherein the reusable frame member is detachably connectable by mechanical attachment means to the single-use absorbent device.

3. The reusable frame member of claim 2, wherein the impervious sublayer is detachably connectable by mechanical attachment means to the single-use absorbent device.

4. The reusable frame member of claim 2, wherein the mechanical attachment means comprises peripheral lips for receiving and restraining the single-use absorbent device in the central void.

5. The reusable frame member of claim 4, wherein the reusable frame member forms a plane, wherein the central void and the single-use absorbent device each include longitudinal sides, wherein the peripheral lips are formed by a layer of material within the outer shaping member having margins abutting the longitudinal sides of the central void, wherein the margins can be lifted away from the plane of the reusable frame member to form pockets for receiving the longitudinal sides of the single-use absorbent device.

6. The reusable frame member of claim 1, wherein the central void is a depression in the outer shaping member having a smaller thickness than the remainder of the outer shaping member.

7. The reusable frame member of claim 1, wherein the central void has a width of 5 cm.

8. The reusable frame member of claim 1, wherein the central void has a depth of about 2 mm or greater, a width of about 40 mm or greater, a length of about 60 mm or greater, and wherein the outer shaping member has a width of at about 50 mm or greater.

9. The reusable frame member of claim 1, wherein the single-use device has a width and a length and wherein the central void has a width and length equal to or greater than the width and the length, respectively, of the single-use absorbent device.

10. The reusable frame member of claim 9, wherein the central void has a width greater than that of the single-use absorbent device such that a gap exists between the longitudinal sides of the central void and the longitudinal sides of the single-use absorbent device when the single-use absorbent device is placed centrally in the central void.

11. The reusable frame member of claim 1, further comprising a central rising member.

12. The reusable frame member of claim 11, wherein the central rising member is disposed within the central void of the outer shaping member.

13. The reusable frame member of claim 11, wherein the central rising member is disposed below the wicking barrier and at least partially overlaps with the central void of the outer shaping member.

14. The reusable frame member of claim 1, wherein the outer shaping member has a thickness of at least about 1 mm.

15. A composite absorbent article comprising the reusable frame member of claim 1 and a single-use absorbent device detachably connected to the reusable frame member and disposed substantially over the central void of the reusable frame member.

16. A package comprising at least one reusable frame member according to claim 1 and a plurality of single-use absorbent devices for use with the reusable frame member, each single-use absorbent device comprising release paper disposed over an adhesive on the garment-side surface of the single-use absorbent device.

17. The reusable frame member of claim 1, wherein the outer shaping member comprises a flexible foam.

18. The reusable frame member of claim 1, additionally comprising attachment means to detachably connect the single-use absorbent device to the outer shaping member, wherein the attachment means comprises a mechanical fastener.

19. The reusable frame member of claim 1, additionally comprising attachment means to detachably connect the single-use absorbent device to the outer shaping member, wherein the attachment means comprises at least one of a snaps, a hook and loop fastener, and a magnetic fastener.

20. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:
   a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and
   b) a liquid impervious sublayer attached to the outer shaping member and extending beneath at least a portion of the central void,
   wherein the impervious sublayer is visible through the central void prior to use when viewed from above the body-side surface of the frame member.

21. The reusable frame member of claim 20, wherein the impervious sublayer is detachably connectable to the single-use absorbent device.

22. The reusable frame member of claim 21, wherein the impervious sublayer is detachably connectable to the single-use absorbent device by an adhesive.

23. The reusable frame member of claim 22, wherein the impervious sublayer includes a body-side surface substantially free of adhesive, and wherein the single-use absorbent device comprises the adhesive for attachment to the reusable frame member.

24. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:
   a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and
   b) a liquid impervious sublayer attached to the outer shaping member and extending beneath at least a portion of the central void,
   wherein the central void is a hole that passes through the outer shaping member.

25. The reusable frame member of claim 24, wherein the central void is a longitudinal gap between two separated halves of the outer shaping member.

26. A package comprising at least one reusable frame member according to claim 24 and a plurality of single-use absorbent devices for use with the reusable frame member, each single-use absorbent device comprising release paper disposed over an adhesive on the garment-side surface of the single-use absorbent device.

27. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:
   a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and
   b) a liquid impervious sublayer attached to the outer shaping member and extending beneath at least a portion of the central void,
   wherein the outer shaping member comprises cellulosic fibers and thermoplastic binding material.

28. A package comprising at least one reusable frame member according to claim 27 and a plurality of single-use absorbent devices for use with the reusable frame member, each single-use absorbent device comprising release paper disposed over an adhesive on the garment-side surface of the single-use absorbent device.

29. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:
   a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and b) a liquid impervious sublayer attached to the outer shaping member and extending beneath at least a portion of the central void, wherein the outer shaping member comprises at least one of an airlaid web, coform, crosslinked cellulosic fibers, and fluff pulp.

30. The reusable frame member of claim 1, wherein the outer shaping member comprises a flexible foam.

31. The reusable frame member of claim 29, wherein the outer shaping member comprises a nonwoven web comprising synthetic fibers.

32. The reusable frame member of claim 31, wherein the nonwoven web is a highloft nonwoven.

33. The reusable frame member of claim 31, wherein the outer shaping member comprises a carded web.

34. The reusable frame member of claim 31, wherein the outer shaping member comprises one of a corrugated nonwoven web or a creped nonwoven web, the nonwoven web having a thickness of about 2 mm or greater.

35. The reusable frame member of claim 29, additionally comprising attachment means to detachably connect the single-use absorbent device to the outer shaping member, wherein the attachment means comprise an adhesive.

36. The reusable frame member of claim 29, additionally comprising attachment means to detachably connect the single-use absorbent device to the outer shaping member, wherein the attachment means comprises a mechanical fastener.

37. The reusable frame member of claim 29, additionally comprising attachment means to detachably connect the single-use absorbent device to the outer shaping member, wherein the attachment means comprises at least one of a snaps, a hook and loop fastener, and a magnetic fastener.

38. A package comprising at least one reusable frame member according to claim 29 and a plurality of single-use absorbent devices for use with the reusable frame member, each single-use absorbent device comprising release paper disposed over an adhesive on the garment-side surface of the single-use absorbent device.

39. The reusable frame member of claim 29, wherein the outer shaping member has a thickness of at least about 1 mm.

40. A composite absorbent article comprising the reusable frame member of claim 29 and a single-use absorbent device detachably connected to the reusable frame member and disposed substantially over the central void of the reusable frame member.

41. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:

a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and b) a liquid impervious sublayer attached to the outer shaping member and extending beneath at least a portion of the central void, further comprising indicator means to alert the wearer that the single-use absorbent device needs to be replaced when leakage is likely or when a predetermined quantity of fluid has been absorbed by the single-use absorbent device.

42. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:

a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and b) a liquid impervious sublayer attached to the outer shaping member and extending beneath at least a portion of the central void, wherein the outer shaping member has from about 15 percent to about 60 percent rebound as determined by the ASTM Test Method D3574-91 procedure H.

43. A flexible, reusable frame member attachable to the undergarments of a wearer for receiving a single-use absorbent device, the single-use absorbent device being detachably connectable to the reusable frame member, wherein the reusable frame member and the single-use absorbent device each include a body-side surface and a garment-side surface, the reusable frame member comprising:

a) an outer shaping member comprising a layer of flexible material having a width greater than the width of the single-use absorbent device and comprising a central void therein for receiving at least a portion of the single-use absorbent device, wherein the outer shaping member includes a body-side surface and a garment-side surface and wherein the outer shaping member is protected from premature soiling by at least one of a hydrophobic surface on the outer shaping member and a wicking barrier attached to the body-side surface of the outer shaping member; and b) a liquid impervious sublayer attached to the outer shaping member and extending beneath at least a portion of the central void, wherein the outer shaping member has a compressibility in the range of about 0.7 kPa to about 14 kPa at 50% compression as determined by the ASTM Test Method D3574-91 procedure C.

44. A composite absorbent article having a body side and a garment side, comprising:

a) an outer shaping member having a body-side surface and a garment-side surface and comprising a layer of a resilient material with a central void therein, wherein the central void is a hole passing through the outer shaping member;

b) a liquid impervious wicking barrier disposed on the body-side surface of the outer shaping member;

c) a backsheet disposed on the garment-side surface of the outer shaping member;

d) a detachable single-use absorbent device disposed above the wicking barrier and contained at least partially within the central void of the outer shaping member, the single-use absorbent device having a body-side surface and a garment-side surface; and e) attachment means to detachably connect the single-use absorbent device to the outer shaping member.

45. The composite absorbent article of claim 44, wherein the outer shaping member has a thickness of at least about 1 mm.

46. The composite absorbent article of claim 44, further comprising a central rising member attached to or contained within the single-use absorbent device.

47. The composite absorbent article of claim 44, wherein the single-use absorbent device further comprises a liquid pervious topsheet on the body-side surface thereof.

48. The composite absorbent article of claim 47, wherein the single-use absorbent device further comprises a baffle layer on the garment-side surface thereof.

49. The composite absorbent article of claim 44, wherein the single-use absorbent device comprises cellulosic fibers and thermoplastic binding material.

50. The composite absorbent article of claim 44, wherein the single-use absorbent device is selected from an airlaid web and coform.

51. The composite absorbent article of claim 44, wherein the single-use absorbent device comprises fluff pulp.

52. The composite absorbent article of claim 44, wherein the outer shaping member comprises cellulosic fibers and thermoplastic binding material.

53. The composite absorbent article of claim 44, wherein the outer shaping member comprises at least one of an airlaid web, coform, crosslinked cellulosic fibers, and fluff pulp.

54. The composite absorbent article of claim 44, wherein the outer shaping member comprises a flexible foam.

55. The composite absorbent article of claims 44, wherein the attachment means comprises adhesive.

56. The composite absorbent article of claim 44, wherein the attachment means comprises a mechanical fastener.

57. The composite absorbent article of claim 56, wherein the mechanical fastener comprises at least one of snaps, hook and loop fasteners, and magnetic fasteners.

58. The composite absorbent article of claim 56, wherein the mechanical fastener comprises at least one of tabs in the single-use absorbent device for engaging one or more slots in the reusable frame member and peripheral lips in the outer shaping member forming longitudinal pockets adjacent the central void for receiving the sides of the single-use absorbent device.

59. The composite absorbent article of claim 44, further comprising a central rising member.

60. The composite absorbent article of claim 59, wherein the central rising member is disposed within the central void of the outer shaping member.

61. The composite absorbent article of claim 59, wherein the central rising member is disposed below the wicking a barrier and at least partially overlaps with the central void of the outer shaping member.

62. The composite absorbent article of claim 44, wherein the outer shaping member has from about 15 percent to about 60 percent rebound as determined by the ASTM Test Method D3574-91 procedure H.

63. The composite absorbent article of claim 44, wherein the outer shaping member has a compressibility in the range of about 0.7 kPa to about 14 kPa at 50% compression as determined by the ASTM Test Method D3574-91 procedure C.

64. A method for improving at least one of the body fit and leakage protection of a single-use absorbent device for absorbing body exudates from the body of a wearer, comprising a) attaching a flexible, reusable frame member to the undergarment of the wearer, the frame member comprising an outer shaping member having a body-side surface and a garment-side surface and wherein the outer shaping member comprises a layer of flexible material having a width greater than the width of the single-use absorbent device, a liquid impervious web or film substantially covering one of the body-side surface and garment-side surface of the outer shaping member, and a central void for receiving at least a portion of the single-use absorbent device;

b) attaching the single-use absorbent device to the body-side surface of the frame member, such that a portion of the absorbent device extends into the central void of the outer shaping member.

65. The method of claim 64, wherein attaching the single-use absorbent device to the frame member is performed with adhesive means.

66. The method of claim 64, wherein attaching the single-use absorbent device to the frame member is performed with mechanical attachment means.

67. A method for economically providing protection of undergarments from exudates from the body of a wearer, comprising:

a) providing a fresh single-use absorbent device having a width and a garment-side surface, comprising a topsheet, a baffle layer attached to the topsheet, an absorbent core between the topsheet and the baffle layer, and adhesive on the baffle layer;

b) attaching a flexible, reusable frame member to the undergarment of the wearer, the frame member comprising an outer shaping member having a body-side surface and a garment-side surface and wherein the outer shaping member comprises a layer of flexible material having a width greater than the width of the single-use absorbent device, a liquid impervious web or film covering at least a portion of one of the body-side surface or garment-side surface of the outer shaping member, the outer shaping member having a central void for receiving at least a portion of the single-use absorbent device;

c) contacting the adhesive on the baffle layer of the fresh single-use absorbent device to the reusable frame member such that the single-use absorbent device is disposed over the central void and attached to the reusable frame member;

d) bringing the undergarments toward the body of the wearer such that the single-use absorbent device is in contact with the body of the wearer;

e) detaching the single-use absorbent device from the reusable frame member after a quantity of fluid has been absorbed by the single-use absorbent device, whereby the single-use absorbent device has become used;

f) discarding the used single-use absorbent device;

g) providing a fresh single-use absorbent device; and h) repeating steps ⓒ through (f).

* * * * *